United States Patent
Consalvo et al.

(10) Patent No.: US 7,445,911 B2
(45) Date of Patent: Nov. 4, 2008

(54) ENZYMATIC REACTIONS IN THE PRESENCE OF KETO ACIDS

(75) Inventors: Angelo P. Consalvo, Monroe, NY (US); Nozer M. Mehta, Randolph, NJ (US); William Stern, Tenafly, NJ (US); James P. Gilligan, Union, NJ (US)

(73) Assignee: Unigene Laboratories Inc., Fairfield, NJ (US)

( * ) Notice: Subject to any disclaimer, the term of this patent is extended or adjusted under 35 U.S.C. 154(b) by 293 days.

(21) Appl. No.: 11/285,136

(22) Filed: Nov. 22, 2005

(65) Prior Publication Data

US 2006/0127995 A1     Jun. 15, 2006

Related U.S. Application Data

(60) Provisional application No. 60/630,748, filed on Nov. 24, 2004.

(51) Int. Cl.
  *C12P 21/06*     (2006.01)
(52) U.S. Cl. ...................................... 435/68.1
(58) Field of Classification Search .................. None
  See application file for complete search history.

(56) References Cited

U.S. PATENT DOCUMENTS

| | | | |
|---|---|---|---|
| 4,708,934 A | 11/1987 | Gilligan et al. | 435/68 |
| 5,196,316 A | 3/1993 | Iwasaki et al. | 435/69.1 |
| 6,103,495 A | 8/2000 | Mehta et al. | 435/69.1 |
| 2004/0197323 A1 | 10/2004 | Mehta et al. | 424/130.1 |
| 2005/0221442 A1 | 10/2005 | Mehta et al. | 435/69.4 |

FOREIGN PATENT DOCUMENTS

| EP | 0 308 067 | 3/1989 |
|---|---|---|
| EP | 0 382 403 | 8/1990 |

OTHER PUBLICATIONS

Merkler et al., Archives of Biochemistry and Biophysics, vol. 330, No. 2, pp. 430-434 (Jun. 15, 1996).
Miller et al., "Characterization of a Bifunctional Peptidylglycine α-Amidating Enzyme Expressed in Chinese Hamster Ovary Cells", Archives of Biochemistry and Biophysics, vol. 298, No. 2, pp. 280-388 (Nov. 1, 1992).
Marth V.L. Ray, et al., "Production of Recombinant Salmon Calcitonin by *In Vitro* Amidation of an *Escherichia coli* Produced Precursor Peptide", Biotechnology, vol. 11, pp. 64-70 (Jan. 1993).
Mizuno et al., Biochemical and Biophysical Research Communications, vol. 148, No. 2, pp. 546-552 (Oct. 29, 1987).
International Search Report and the Written Opinion of the International Searching Authority dated Dec. 15, 2006, of corresponding International Application No. PCT/US05/42765.

*Primary Examiner*—Herbert J. Lilling
(74) *Attorney, Agent, or Firm*—Ostrolenk, Faber, Gerb & Soffen, LLP

(57) ABSTRACT

Conversion in vitro of X-Gly to X-alpha-hydroxy-Gly or X—$NH_2$ (X being a peptide or any other compound having a carbonyl group capable of forming a covalent bond with glycine) is accomplished enzymatically in the presence of keto acids, or salts or esters thereof, to provide a good yield without the necessity of catalase or similar enzymatic reaction enhancers. Peptidylglycine α-amidating monooxygenase (PAM) is a preferred enzyme for catalyzing the conversion. Alternatively, peptidylglycine α-hydroxylating monooxygenase (PHM) is utilized to convert X-Gly to X-alpha-hydroxy-Gly which may be recovered, or optionally may be simultaneously or sequentially converted to an amide by either a Lewis base or action of the enzyme peptidyl α-hydroxyglycine α-amidating lyase (PAL). Both PHM and PAL are functional domains of PAM.

38 Claims, No Drawings

ENZYMATIC REACTIONS IN THE PRESENCE OF KETO ACIDS

The present application claims priority under 35 U.S.C. §119 of Provisional Application Ser. No. 60/630,748 filed Nov. 24, 2004.

FIELD OF THE INVENTION

The present invention relates to enzymatic conversion of X-Gly to X-alpha-hydroxy-Gly or X—$NH_2$ (X being a peptide or any chemical compound having a carbonyl group to which a glycine group can be covalently attached) in the presence of certain reaction-enhancing compounds. In preferred embodiments, these reaction-enhancing compounds are keto acids (or salts or esters thereof) which may beneficially be used in lieu of catalase, a typical component of prior art enzymatic reactions of these types, such as amidation reactions.

DESCRIPTION OF THE RELATED ART

Numerous human hormones, growth factors, cytokines, neurotransmitters derivatized fatty acids, and other important biological compounds have amino acid or peptide as a substantial part of their molecular structures. Many diseases respond positively to raising the level of these biological compounds in patients. Therapeutically effective amount of such biologically relevant compounds may be administered to patients in a variety of ways. Thus, efficient cost-effective manufacturing processes for such compounds are very important. This is especially true when the biological compounds are prepared in dosage form for oral delivery, a usually preferred mode of administration despite lower bioavailability relative to other modes of administration.

Mammalian cells and other eukaryotes can perform certain post-translational processing procedures, while prokaryotes cannot. Certain prokaryotes, such as *E. coli*, are widely employed as hosts for the production of mammalian proteins via recombinant DNA (rDNA) technology because they can be readily grown in batch fermentation procedures and because they are genetically well-characterized. However, many mammalian proteins require some type of post-translational processing. If these proteins are produced by genetic engineering of *E. coli*, for example, the post-translational processing must often be accomplished using complex, in vitro chemical procedures which are cost-prohibitive for large-scale production applications. Even when peptides are recombinantly produced using mammalian hosts, it is often desirable to efficiently produce a precursor which is only later subjected to further modification.

One type of such further processing activity involves the specific amidation of the carboxy-terminal amino acid of a peptide or protein. Many naturally-occurring hormones and peptides contain such a modification, which is often essential if the protein is to be biologically active. An example is calcitonin, where the substitution of a non-amidated proline residue for the amidated proline of the native form results in a very significant reduction in biological activity. Other biological peptides requiring post-translational amidation for full activity include but are not limited to growth hormone releasing factor, other calcitonins, calcitonin gene-related peptide, secretin, Peptide YY and the like.

The specific amidation of the carboxy-terminal amino acid of a protein is frequently catalyzed by alpha-amidating enzymes. The polypeptide sequences for many important biological proteins which require amidation for maximal efficacy, may be manufactured, for example, by genetic engineering techniques. However, the important and sometimes essential carboxy terminal amidation must often be performed in vitro. It is desirable to avoid costly and cumbersome chemical amidation techniques at this point, and is therefore desirable to utilize an amidating enzyme to perform the specific amidation.

Peptidylglycine α-amidating monooxygenase (PAM) catalyzes the conversion of a peptide substrate to an amidated peptide product. The conversion is a two-step reaction. PAM has two catalytic domains: peptidylglycine α-hydroxylating monooxygenase (PHM) catalyzes Step 1 (conversion of substrate to intermediate) and peptidylglycine α-hydroxyglycine α-amidating lyase (PAL) which catalyzes Step 2 (conversion of intermediate to product). Full length PAM catalyzes both steps.

In nature, approximately 50% of peptide hormones and neurotransmitters are amidated by PAM in the foregoing manner. PAM activity has been recognized in numerous diverse species, and tends to have significant structural homology among species as diverse as rat, cow and frog. It is also known that PAM's function, substrate and cofactors are similar (frequently identical) across species. The substrate is a compound, often a peptide, having a glycine residue with a free carboxyl group. PAM-catalyzed amidation reactions are well known in the art. For example, one is described in detail in U.S. Pat. No. 6,103,495 where a peptidylglycine α-amidating monooxygenase is used to catalyze the conversion of a glycine-extended salmon calcitonin precursor to authentic salmon calcitonin amidated at its C-terminus (i.e., having an amino group in place of the precursor's C-terminal glycine).

The activity of PAM is rapidly diminished in the course of an amidation reaction due to inactivation of the enzyme. To prevent such inactivation, prior art enzymatic amidation reactions typically require a secondary enzyme (for example catalase or horse radish peroxidase) for good conversion and reaction yields. This however, negatively impacts the cost and efficiency of the process, and is also undesirable from a regulatory standpoint. For example, catalase is a large protein that is a difficult to purify, and which may be contaminated by undesirable proteases which can attack any of product, precursor and/or enzyme during amidation reactions. Proteins that co-purify with catalase may also contaminate the final product beyond regulatory standards in the case of pharmaceutical products. Additionally, when catalase is from an animal source, or when animal components are used in catalase manufacture, special care must be taken to avoid transmissable spongiform encephalophathies.

SUMMARY OF THE INVENTION

It is accordingly an object of the present invention to provide efficient, high yield, low-cost enzymatic amidation reactions wherein catalase or other enzymatic scavengers may be substantially reduced relative to the prior art, and preferably eliminated altogether. It is another object to provide amidated biological compounds manufactured in accordance with the foregoing reaction methods.

In one aspect, the invention provides a method for the in vitro production of an amidated product, said method comprising reacting a precursor having a glycine residue, in free acid form and attached to a carbonyl group, in the presence of (A) peptidylglycine alpha-amidating monooxygenase and (B) a reaction-enhancing compound that is an alpha-keto acid, or salt or ester thereof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid.

In another aspect, the invention provides a method for the in vitro production of an amidated product, said method comprising: forming a hydroxylated intermediate by reacting a precursor having a glycine residue, in free acid form and attached to a carbonyl group, in the presence of (i) peptidylglycine alpha-hydroxylating monooxygenase and (ii) a reaction-enhancing compound that is an alpha-keto acid, or salt or ester thereof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid; and simultaneously or subsequently reacting said intermediate in the presence of either a Lewis base or peptidyl alpha-hydroxyglycine alpha-amidating lyase.

In another embodiment, the invention provides a method for enhancing the bioavailability of a peptide pharmaceutical agent wherein said agent is amidated at a location that is not naturally amidated, said non-natural amidation being accomplished by reacting a precursor having a glycine residue, in free acid, form at a position where amidation is desired in the presence of (A) peptidylglycine alpha-amidating monooxygenase and (B) a reaction-enhancing compound that is an alpha-keto acid, or salt or ester therof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid.

In another aspect, the invention provides A method for enhancing the bioavailability of a peptide pharmaceutical agent wherein said agent is amidated at a location that is not naturally amidated, said non-natural amidation being accomplished by (A) reacting a precursor having a glycine residue, in free acid form and attached to a carbonyl group at a position where amidation is desired, in the presence of (i) peptidylglycine alpha-hydroxylating monooxygenase and (ii) a reaction-enhancing compound that is an alpha-keto acid, or salt or ester therof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid, thus forming a hydroxylated intermediate; and (B) simultaneously or subsequently reacting said intermediate with either a Lewis base or peptidyl alpha-hydroxyglycine alpha-amidating lyase.

In one embodiment of the above methods, the reaction-enhancing compound is an α-keto-acid salt. In another, the reaction-enhancing compound is an α-keto-acid ester. In yet another embodiment, the reaction-enhancing compound is an α-keto-acid.

In one embodiment, R (in the molecular structure of the reaction-enhancing compound) is aryl (preferably phenyl). In another embodiment, R is a C1-C4 hydrocarbon, preferably a C1-C4 alkyl. Straight-chain R groups may be slightly more effective than corresponding branched-chain R groups.

The invention also provides amidated products that have been prepared in accordance with any of the methods mentioned herein.

DETAILED DESCRIPTION OF THE INVENTION

The present invention is applicable to the manufacture of any compound where it is desirable to have an amide group. Because the enzymes discussed herein recognize peptides having glycine residues, the present invention is useful for the amidation of such structures even when they are part of larger molecules that include, at other locations, non-natural or modified amino acids, or amino acid derivatives such as protecting groups or the like. Even compounds having, as part of their molecular structures, non-peptide regions, should benefit from the present invention so long as there is a glycine recognizable by the enzymes utilized herein.

The enzymes which catalyze the reactions herein are believed to recognize any precursor substrate having a glycine residue that is in free acid form (ie having a free carboxyl group) and is attached to a carbonyl group. See, for example, Merkler et al., *Archives of Biochemistry and Biophysics*, 1966, Vol. 330, No. 2, 430-434 (glycine extended fatty acid substrates); and U.S. Pat. No. 6,103,495 (salmon calcitonin with C-terminal glycine in position of amide-forming amino group in natural salmon calcitonin, used as substrate for amidation to salmon calcitonin). Accordingly, it is expected that any enzymatic amidation of any substrate utilizing the amidating enzymes discussed herein may benefit from the present invention which enhances that enzymatic amidation with substitutes for prior art catalase (or other reaction-enhancing compound of the prior art such as a scavenging enzyme). The same should be true of PHM-catalyzed reactions, PHM being one of the functional domains of PAM.

There are numerous pharmaceutical agents, including not only natural hormones and neurotransmitters, but also pharmaceutically active truncates and modifications thereof, or derivatized fatty acids, which are more biologically active when amidated. Even when biological activity is not necessarily increased, amidating a pharmaceutical agent may desirably increase oral bioavailability relative to utilizing that agent in free-acid form. See United States Patent Publication Number 20040197323 published Oct. 7, 2004 (publication of U.S. patent application Ser. No. 10/761,481 by Mehta et al), the disclosure of which is incorporated herein by reference. Those of skill in the art may appreciate other reasons for amidating a peptide or other compound as taught herein. The present invention is believed to enhance PAM-catalyzed and PHM-catalyzed reactions, regardless of product or substrate chosen, so long as the substrate is one recognized by PAM or PHM.

Peptidylglycine α-amidating monooxygenase (PAM) and its two catalytic domains, peptidylglycine α-hydroxylating monooxygenase (PHM) and peptidylglycine α-hydroxyglycine α-amidating lyase (PAL) are reported in the literature. The art has also reported preferred reaction conditions, cofactors and the like. One particular example of an amidation, and purification of amidated product, is reported herein. A primary improvement of the present invention is that catalase which is commonly used in prior art amidations can now be replaced with certain α-keto acids (or salts or esters thereof).

Without intending to be bound by theory, it is believed that the enzymatic reactions discussed herein undesirably produce hydrogen peroxide as a by-product which can have negative effects on the enzymatic reaction, and/or the recoverable product yield. It is believed that, in the prior art, catalase may have acted as a peroxide scavenger to minimize the negative effect of any hydrogen peroxide that is formed.

Again without intending to be bound by theory, it is believed that the α-keto acids (or salts or esters thereof) of the present invention effectively perform that role of peroxide scavenger without the necessity of catalase or other scavenging enzymes. It is believed that, for example, an α-keto acid could react with hydrogen peroxide in the following manner:

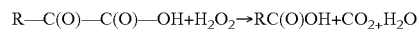

When pyruvic acid is used as the α-keto acid, it is hypothesized that it reacts with hydrogen peroxide to produce acetic acid, water and carbon dioxide.

Because the R group is unchanged in this reaction, a large number of R moieties is possible. Applicants have tested a number of keto acids (or corresponding esters or salts thereof), and have reported their efficacy in Table 1 below for the amidation of recombinant human parathyroid hormone truncate (first 31 amino acids of PTH followed by C-terminal glycine). Amidation using catalase is also reported in the footnotes to Table 1. The conversions to amidated product are not directly comparable in Table 1 because different concentrations of the reaction-enhancing keto acids (or salts or esters thereof) are utilized. A preferred concentration was chosen for each compound. Also, separate controls are therefore used with respect to each of the compounds tested in Table 1, so that each compound's performance may be compared to its corresponding control. As noted, three of the tested compounds did not outperform the corresponding control. The control values that are set forth in Table 1 are typical values observed for amidation of rhPTH(1-31)Gly32-OH in the absence of the reaction-enhancing compounds of the invention.

Amidation Reactions with α-Keto Acids/Esters

Set forth below are some of the specifics of the reactions that were performed to test the efficacy of various keto acids (or salts or esters thereof).

To determine the information in Table 1 below, stock solutions of all reagents were prepared in water. Amidations were carried out under the following conditions: 4 mg/mL rhPTH (1-31)Gly32-OH, 30 mM 2-morpholinoethanesulfonic acid (MES) pH [6.3-6.5], 0.5 µM cupric sulfate, 5 mM potassium iodide, 2 mM ascorbate, [0-1%] ethanol and 15,000 U/mL PAM. All reactions were incubated for 4 hours at 37° C. Reagents were added in the following order: rhPTH(1-31) Gly32-OH, water, MES, potassium iodide, ethanol, cupric sulfate, α-keto acid or ester, ascorbate and PAM. All reactions were acidified to pH 2.0 with 6% trifluoroacetic acid and analyzed by CEX-HPLC (area %) to detect formation of the desired product rhPTH(1-31)NH$_2$. The results were as follows in Table 1.

TABLE 1

α-Amidation of rhPTH(1-31)Gly32-OH to rhPHT(1-31)-NH2 in the Presence of α-Keto Acids/Esters

| α-Keto Acid/Ester | Structure | Concentration (mM) | % Conversion | % Conversion - Control (no compound of invention) |
|---|---|---|---|---|
| Sodium pyruvate | $CH_3COCO_2Na$ | 8 | 95 | 60 |
| Ethyl pyruvate | $CH_3COCO_2CH_2CH_3$ | 50 | 89 | 56 |
| Pyruvic acid | $CH_3COCO_2H$ | 6 | 86[a] | 56[a] |
| Methyl pyruvate | $CH_3COCO_2CH_3$ | 50 | 86 | 58 |
| Benzoylformic acid | $C_6H_5COCO_2H$ | 10 | 82 | 67 |
| 2-Ketobutyric acid, sodium salt | $CH_3CH_2COCO_2Na$ | 16 | 96 | 60 |
| 3-Methyl-2-oxobutanoic acid, sodium salt | $(CH_3)_2CHCOCO_2Na$ | 64 | 78 | 38 |
| 2-Keto glutaric acid, sodium salt | $HO_2CCH_2CH_2COCO_2Na$ | 10 | 76 | 58 |
| 3-Methyl-2-oxopentanoic acid, sodium salt | $C_2H_5CH(CH_3)COCO_2Na$ | 10-150 | ≦61 | 61 |
| 4-Methyl-2-oxopentanoic acid, sodium salt | $(CH_3)_2CHCH_2COCO_2Na$ | 10-150 | <48 | 48 |
| Phenyl Pyruvate, sodium salt | $C_6H_5CH_2COCO_2Na$ | 0.1-100 | <58 | 58 |

α-Amidations were carried out under the following conditions: 4 mg/mL rhPTH(1-31)Gly32-OH, 30 mM MES pH [6.3-6.5], 0.5 µM cupric sulfate, 5 mM potassium iodide, 2 mM ascorbate, [0-1%] ethanol and 15,000 U/mL PAM. Reactions were incubated for 4 hours at 37° C.
Amidations carried out under similar conditions with catalase (*Aspergillus niger*) as the peroxide scavenger typically resulted in >90% conversion of rhPTH(1-31)Gly32-OH to rhPTH(1-31)-NH2.
[a]These data represent the average of triplicate values.

As shown in Table 1, salts and esters of the α-keto acids tended to perform similarly to the corresponding α-keto acids. Larger R groups tended not to perform as well as smaller R groups (C1-C4 being preferred), except that aromatic groups tended to perform well when located in a electron withdrawing position. Straight-chain compounds tended to perform a little better than corresponding branched compounds. It is expected that the hydrocarbon moieties may be halogenated or hydrogenated without significantly impairing function. As shown, the effective compounds perform quite well and are thus suitable alternatives to prior art catalase, thus avoiding the shortcomings of catalase discussed above.

Set forth below are some detailed process steps for amidating a substrate and purifying the resulting product in accordance with the invention.

EXAMPLE 1

Conversion Of Glycine-Extended Parathyroid Hormone Fragment To Amidated Counterpart Using Peptidylglycine α-amidating Monooxygenase.

Amidation of rhPTH(1-34)Gly35-OH Using Pyruvate

The components and final concentrations used for amidation of rhPTH(1-34)Gly35-OH are shown in the Table 2. A brief description of the amidation follows.

TABLE 2

α-Amidation of rhPTH(1-34)Gly35-OH

| Reagent | Final Concentration |
| --- | --- |
| rhPTH(1-34)Gly35-OH | 2 mg/mL |
| 250 mM MES pH 6.3 | 30 mM |
| 3 mM Cupric Sulfate | 0.5 μM |
| 100 mM Sodium Ascorbate | 2 mM |
| Oxygen | The dissolved oxygen concentration is maintained at or near saturation. |
| 400 mM Sodium Pyruvate | 8 mM |
| 250 mM Potassium Iodide | 5 mM |
| 190 Proof Ethanol | 1% |
| PAM | 30,000 U/mL |

Approximately 12.4 grams of rhPTH(1-34)Gly35-OH in 1,900 mL of 25 mM MES, 200 mM NaCl pH 6.0 was charged into a glass vessel fitted with an agitator and gas sparger.

To this solution, the following components were added in the order listed: 3,025 mL water, 741 mL 250 mM MES pH 6.3, 1.03 mL 3 mM cupric sulfate, 124 mL potassium iodide, 62 mL 190 proof ethanol, 124 mL 400 mM sodium pyruvate and 124 mL 100 mM sodium ascorbate.

The reaction vessel was placed into a water-bath and the reaction mixture was heated to 25-27° C. with stirring.

The pH of the reaction mixture was adjusted by to 5.8 with 21 mL of 2 M HCl. Oxygen sparging was initiated; the sparging rate was adjusted to avoid excessive foaming of the reaction mixture.

47 mL of PAM was added and the reaction mixture was incubated at 25-27° C. for 4 hours and 35 minutes (oxygen sparging was performed throughout the incubation period).

The reaction mixture was acidified to pH 2.4 with 74 mL of 2 M HCl.

The PAM enzyme may be obtained as described in Miller et al., ABB 298: 380-388 (1992) U.S. Pat. No. 4,708,934, European publication 0 308 067 and 0 382 403, and Biotechnology Vol. II (1993) pp. 64-70, the disclosures of which are hereby incorporated by reference. The PAM enzyme may also be obtained from a PAM-expressing cell line internally designated UGL 73-26/M MWCB 00 which was deposited with the American Type Culture Collection (ATCC), 10801 University Boulevard, Manassas Va., 20110-2209, U.S.A. as ATCC accession number PTA-6784 pursuant to the Budapest Treaty on the International Recognition of Deposits of Microorganisms for Purposes of Patent Procedure. This deposited cell line is subject to the Regulations promulgated under this Treaty, and samples will be made available at the time, and under the conditions required by, the Treaty, and in compliance with the patent laws and regulations of the Treaty signatories. For example, upon issuance of a U.S. patent based on this application or any other U.S. application claiming priority hereof or making reference hereto, all restrictions upon availability of the deposited material will be irrevocably removed to the extent required by the Budapest Treaty or by 35 U.S.C. §112.

The glycine extended precursor may be produced by fermentation in a manner analogous to that described in U.S. Pat. No. 6,103,495, Examples 1-2 and purified as described in U.S. Pat. No. 6,103,495, Example 3 prior to amidation. It may also be produced in accordance with U.S. Patent Publication U.S. 2005/0221442 (U.S. application Ser. No. 11/076,260). The disclosures of the foregoing are hereby incorporated by reference.

In instances where the enzyme used for amidation is peptidyl glycine alpha.-hydroxylating monooxygenase (PHM), the same reaction mixture is used as that described above, substituting PHM for PAM. In addition, at the end of the 4 to 6 hour incubation period, the pH of the reaction mixture is increased by the addition of base to between 8 and 9. The reaction mixture is agitated for an additional 4 to 8 hours prior to terminating the reaction. PHM may be obtained by expressing only the N-terminal portion of PAM (about the first 40 dKa). See e.g. Mizuno et al. BBRC Vol. 148, No. 2, pp. 546-52 (1987) the disclosure of which (as it relates to Mizuno's "AE 1" is incorporated herein by reference. Frog skin is known to express PHM naturally.

EXAMPLE 2

Post-Amidation Purification

Cation Exchange (CEX) Chromatography

Purification of rhPTH(1-34)-$NH_2$ from residual rhPTH(1-34)Gly35-OH was achieved using CEX chromatography. A brief description of the CEX chromatography method is described below. The acidified amidation output was loaded onto a Toyopearl SP650M (Tosoh Bioscience LLC) column, 9 cm×19 cm, equilibrated with 25 mM MES pH 6.5. The column was operated at 180 cm/hr and the UV absorbance of the column effluent was monitored at 280 nm. The column was washed with 25 mM MES pH 6.5 until the pH of the column effluent pH returned to 6.5. The column was washed with 25 mM MES, 80 mM NaCl pH 6.5 until the wash peak completely eluted and a stable UV baseline was achieved. The product, rPTH(1-34)-$NH_2$, was eluted from the column with 25 mM MES, 200 mM NaCl pH 6.5. The entire UV peak was collected; fractions were screened by RP-HPLC to determine pooling criteria.

Reversed-Phase (RP) Chromatography

RP chromatography was utilized to exchange the salt form of the peptide from chloride to acetate; RP chromatography provides marginal purification of the peptide. The CEX chromatography output was diluted with 3 volumes of 333 mM sodium acetate and mixed thoroughly. The mixture was allowed to stand for 75 minutes at room temperature prior to loading. The acetate diluted sample was loaded onto a Amberchrom CG300 M (Tosoh Bioscience LLC) column, 6 cm×17 cm, equilibrated with 250 mM sodium acetate pH 7.5. The column was operated at 180 cm/hr and the UV absorbance of the column effluent was monitored at 280 nm. The column was washed with 250 mM sodium acetate pH 7.5 for 60 minutes. The column was equilibrated in 0.1% acetic acid. The product, rhPTH(1-34)-$NH_2$, was eluted from the column with 0.1% acetic acid, 40% ethanol. The entire UV peak was collected.

Characterization of rhPTH(1-34)-$NH_2$

The RP chromatography output was concentrated to a white flocculent powder by lyophilization, yielding 11.8 grams (95% overall yield from amidation) of rhPTH(1-34)-$NH_2$. The molecular mass for rhPTH(1-34)-$NH_2$ was determined to be 4,116.9 Da by electrospray ionization mass spectrometry (ESI-MS), which was consistent with the calculated average molecular mass of 4,116.8 Da.

Although the present invention has been described in relation to particular embodiments thereof, many other variations and modifications and other uses will be apparent to those skilled in the art. The present invention therefore is not limited by the specific disclosure herein, but only by the appended claims.

What is claimed is:

1. A method for the in vitro production of an amidated product, said method comprising reacting a precursor having a glycine residue, in free acid form and attached to a carbonyl group, in the presence of (A) peptidylglycine alpha-amidating monooxygenase and (B) a reaction-enhancing compound that is an alpha-keto acid, or salt or ester therof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid.

2. The method of claim 1 wherein said reaction-enhancing compound is an alpha-keto acid salt.

3. The method of claim 1 wherein said reaction-enhancing compound is an alpha-keto acid ester.

4. The method of claim 1 wherein said reaction-enhancing compound is an alpha-keto acid.

5. The method of claim 1 wherein R is aryl.

6. The method of claim 5 wherein R is phenyl.

7. The method of claim 1 wherein R is a C1-C4 hydrocarbon.

8. The method of claim 1 wherein R is a C1-C4 alkyl.

9. The method of claim 1 wherein said reaction-enhancing compound is selected from the group consisting of ethyl pyruvate, pyruvic acid or salt thereof, methyl pyruvate, benzoyl formic acid or salt thereof, 2-ketobutyric acid or salt thereof, 3-methyl-2-oxobutanoic acid or salt thereof, and 2-keto glutaric acid or salt thereof.

10. The method of claim 1 wherein said reaction enhancing compound is selected from the group consisting pyruvic acid and sodium pyruvate.

11. A method for the in vitro production of an amidated product said method comprising:
(A) forming a hydroxylated intermediate by reacting a precursor having a glycine residue, in free acid form and attached to a carbonyl group, in the presence of (i) peptidylglycine alpha-hydroxylating monooxygenase and (ii) a reaction-enhancing compound that is an alpha-keto acid, or salt or ester thereof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid; and
(B) simultaneously or subsequently reacting said intermediate with either a Lewis base or peptidyl alpha-hydroxyglycine alpha-amidating lyase.

12. The method of claim 11 wherein said reaction-enhancing compound is an alpha-keto acid salt.

13. The method of claim 11 wherein said reaction-enhancing compound is an alpha-keto acid ester.

14. The method of claim 11 wherein said reaction-enhancing compound is an alpha-keto acid.

15. The method of claim 11 wherein R is aryl.

16. The method of claim 15 wherein R is phenyl.

17. The method of claim 11 wherein R is a C1-C4 hydrocarbon.

18. The method of claim 11 wherein R is a C1-C4 alkyl.

19. The method of claim 11 wherein said reaction-enhancing compound is selected from the group consisting of ethyl pyruvate, pyruvic acid or salt thereof, methyl pyruvate, benzoyl formic acid or salt thereof, 2-ketobutyric acid or salt thereof, 3-methyl-2-oxobutanoic acid or salt thereof, and 2-keto glutaric acid or salt thereof.

20. The method of claim 11 wherein said reaction enhancing compound is selected from the group consisting of pyruvic acid and sodium pyruvate.

21. The method of claim 1 wherein said product is an amidated analog of a natural peptide that is not naturally amidated.

22. The method of claim 11 wherein said product is an amidated analog of a natural peptide that is not naturally amidated.

23. The method of claim 1 wherein said product is an analog of a naturally amidated peptide that is additionally amidated at a location where said natural peptide is not amidated.

24. The method of claim 11 wherein said product is an analog of a naturally amidated peptide that is additionally amidated at a location where said natural peptide is not amidated.

25. A method for enhancing the bioavailability of a peptide pharmaceutical agent wherein said agent is amidated at a location that is not naturally amidated, said non-natural amidation being accomplished by reacting a precursor having a glycine residue, in free acid, form at a position where amidation is desired in the presence of (A) peptidylglycine alpha-amidating monooxygenase and (B) a reaction-enhancing compound that is an alpha-keto acid, or salt or ester therof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid.

26. A method for enhancing the bioavailability of a peptide pharmaceutical agent wherein said agent is amidated at a location that is not naturally amidated, said non-natural amidation being accomplished by (A) reacting a precursor having a glycine residue, in free acid form and attached to a carbonyl group at a position where amidation is desired, in the presence of (i) peptidylglycine alpha-hydroxylating monooxygenase and (ii) a reaction-enhancing compound that is an alpha-keto acid, or salt or ester therof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid, thus forming a hydroxylated intermediate; and
(B) simultaneously or subsequently reacting said intermediate with either a Lewis base or peptidyl alpha-hydroxyglycine alpha-amidating lyase.

27. The method of claim 1 wherein said product is a peptide.

28. The method of claim 11 wherein said product is a peptide.

29. A method for the in vitro production of an alpha-hydroxy-glycine product said method comprising reacting a precursor having a glycine residue, in free acid form and attached to a carbonyl group, in the presence of (i) peptidylglycine alpha-hydroxylating monooxygenase and (ii) a reaction-enhancing compound that is an alpha-keto acid, or salt or ester thereof, wherein said alpha-keto acid has the molecular structure RC(O)C(O)OH, and wherein R is selected from the group consisting of aryl, a C1-C4 hydrocarbon moiety, a halogenated or hydroxylated C1-C4 hydrocarbon moiety, and a C1-C4 carboxylic acid.

30. The method of claim 29 wherein said reaction-enhancing compound is an alpha-keto acid salt.

31. The method of claim 29 wherein said reaction-enhancing compound is an alpha-keto acid ester.

32. The method of claim 29 wherein said reaction-enhancing compound is an alpha-keto acid.

33. The method of claim 29 wherein R is aryl.

34. The method of claim 33 wherein R is phenyl.

35. The method of claim 29 wherein R is a C1-C4 hydrocarbon.

36. The method of claim 29 wherein R is a C1-C4 alkyl.

37. The method of claim 29 wherein said reaction-enhancing compound is selected from the group consisting of ethyl pyruvate, pyruvic acid or salt thereof, methyl pyruvate, benzoyl formic acid or salt thereof, 2-ketobutyric acid or salt thereof, 3-methyl-2-oxobutanoic acid or salt thereof, and 2-keto glutaric acid or salt thereof.

38. The method of claim 29 wherein said reaction enhancing compound is selected from the group consisting of pyruvic acid and sodium pyruvate.

* * * * *